US010835306B2

(12) United States Patent
Franke et al.

(10) Patent No.: US 10,835,306 B2
(45) Date of Patent: *Nov. 17, 2020

(54) SYSTEMS AND METHODS FOR ASSESSING AND TREATING TISSUE

(71) Applicant: Boston Scientific Scimed, Inc., Maple Grove, MN (US)

(72) Inventors: Manfred Franke, Cleveland, OH (US); Bryan Allen Clark, Forest Lake, MN (US); Aiden Flanagan, Kilcolgan (IE); Juan Hincapie Ordonez, Maple Grove, MN (US); Jason J. Hamann, Blaine, MN (US); Allan Shuros, St. Paul, MN (US)

(73) Assignee: Boston Scientifique Scimed, Inc., Maple Grove, MN (US)

( * ) Notice: Subject to any disclaimer, the term of this patent is extended or adjusted under 35 U.S.C. 154(b) by 173 days.

This patent is subject to a terminal disclaimer.

(21) Appl. No.: 15/956,938

(22) Filed: Apr. 19, 2018

(65) Prior Publication Data
US 2018/0235687 A1    Aug. 23, 2018

Related U.S. Application Data

(63) Continuation of application No. 14/658,676, filed on Mar. 16, 2015, now Pat. No. 9,974,597.

(Continued)

(51) Int. Cl.
*A61N 1/36* (2006.01)
*A61B 18/14* (2006.01)
(Continued)

(52) U.S. Cl.
CPC ............ *A61B 18/14* (2013.01); *A61B 5/0036* (2018.08); *A61B 18/1206* (2013.01);
(Continued)

(58) Field of Classification Search
CPC ................ A61B 5/4836; A61N 1/3601; A61N 1/36135; A61N 1/36139; A61N 1/365
See application file for complete search history.

(56) References Cited

U.S. PATENT DOCUMENTS 5,972,026 A    10/1999 Laufer et al.
6,083,255 A    7/2000 Laufer et al.
(Continued)

FOREIGN PATENT DOCUMENTS

CN    2836751 Y    11/2006
WO    03/041779 A1    5/2003

OTHER PUBLICATIONS

College of Veterinary Medicine, Michigan State University, "Mechanism of Action of Bronchodilator Drugs", accessed Mar. 29, 2015, <http://cvm.msu.edu/research/research-labs/equine-pulmonary-laboratory/respiratory-diseases/heaves/mechanism-of-action-bronchodilator-drugs> (2 pages).

(Continued)

*Primary Examiner* — Eric D. Bertram
(74) *Attorney, Agent, or Firm* — Bookoff McAndrews, PLLC

(57) ABSTRACT

A medical device including an elongate member having a proximal end configured to be electrically coupled to an energy source, and a distal member disposed at a distal end of the elongate member. The distal member may include a plurality of contact elements configured to deliver stimulating energy to innervated tissue, detect a response from the innervated tissue to the stimulating energy, and deliver therapeutic energy to the innervated tissue based on the response from the innervated tissue.

15 Claims, 5 Drawing Sheets

Related U.S. Application Data

(60) Provisional application No. 61/955,449, filed on Mar. 19, 2014.

(51) Int. Cl.
*A61B 34/20* (2016.01)
*A61B 5/00* (2006.01)
*A61B 18/12* (2006.01)
*A61B 18/00* (2006.01)
*A61B 18/02* (2006.01)
*A61B 17/00* (2006.01)
*A61B 90/00* (2016.01)

(52) U.S. Cl.
CPC .......... *A61B 18/1492* (2013.01); *A61B 34/20* (2016.02); *A61B 5/0031* (2013.01); *A61B 5/4836* (2013.01); *A61B 2017/00039* (2013.01); *A61B 2017/00115* (2013.01); *A61B 2017/00128* (2013.01); *A61B 2018/0016* (2013.01); *A61B 2018/0022* (2013.01); *A61B 2018/00214* (2013.01); *A61B 2018/00267* (2013.01); *A61B 2018/00273* (2013.01); *A61B 2018/00434* (2013.01); *A61B 2018/00541* (2013.01); *A61B 2018/00577* (2013.01); *A61B 2018/00642* (2013.01); *A61B 2018/00654* (2013.01); *A61B 2018/00702* (2013.01); *A61B 2018/00791* (2013.01); *A61B 2018/00839* (2013.01); *A61B 2018/00875* (2013.01); *A61B 2018/0212* (2013.01); *A61B 2018/1407* (2013.01); *A61B 2018/1435* (2013.01); *A61B 2018/1467* (2013.01); *A61B 2034/2061* (2016.02); *A61B 2090/064* (2016.02); *A61B 2090/065* (2016.02); *A61B 2090/3966* (2016.02); *A61B 2562/0261* (2013.01); *A61B 2562/0266* (2013.01)

(56) References Cited

U.S. PATENT DOCUMENTS

| | | |
|---|---|---|
| 6,283,988 B1 | 9/2001 | Laufer et al. |
| 7,027,869 B2 | 4/2006 | Danek et al. |
| 8,226,638 B2 | 7/2012 | Mayse et al. |
| 8,229,564 B2 | 7/2012 | Rezai |
| 8,509,919 B2 | 8/2013 | Yoo et al. |
| 8,942,824 B2 | 1/2015 | Yoo et al. |
| 2004/0122482 A1 | 6/2004 | Tung et al. |
| 2005/0119654 A1* | 6/2005 | Swanson ............... A61B 18/18 606/49 |
| 2006/0224210 A1* | 10/2006 | Stellar .................... A61B 5/05 607/46 |
| 2008/0234782 A1 | 9/2008 | Haugland et al. |
| 2009/0062685 A1 | 3/2009 | Bergethon et al. |
| 2009/0069709 A1* | 3/2009 | Schmitz ............... A61B 5/0488 600/547 |
| 2009/0259274 A1 | 10/2009 | Simon et al. |
| 2010/0063376 A1 | 3/2010 | Kartush |
| 2010/0217347 A1 | 8/2010 | Swoyer et al. |
| 2010/0228318 A1 | 9/2010 | Errico et al. |
| 2011/0301679 A1 | 12/2011 | Rezai et al. |
| 2011/0306851 A1 | 12/2011 | Wang |
| 2011/0319958 A1 | 12/2011 | Simon et al. |
| 2012/0221087 A1 | 8/2012 | Parnis et al. |
| 2012/0265198 A1* | 10/2012 | Crow ................ A61B 18/1492 606/41 |
| 2012/0271277 A1 | 10/2012 | Fischell et al. |
| 2013/0085416 A1 | 4/2013 | Mest |
| 2014/0031808 A1 | 1/2014 | Phan et al. |

OTHER PUBLICATIONS

Undem et al., "The Role of Vagal Afferent Nerves in Chronic Obstructive Pulmonary Disease", 2005, pp. 355-360, vol. 2, Proceedings of the American Thoracic Society (6 pages).

Canning, Brendan J., "Reflex regulation of airway smooth muscle tone", Sep. 2006, pp. 971-985, vol. 101, Journal of Applied Physiology, American Physiological Society (16 pages).

Undem et al., "Autonomic Neural Control of Intrathoracic Airways", Apr. 2012, pp. 1241-1267, vol. 2, Comprehensive Physiology, American Physiological Society (27 pages).

Barnes et al., "Neural and Humoral Control of the Airways", chapter 32 of "Asthma and COPD: Basic Mechanisms and Clinical Management", 2009, pp. 381-388, 2nd Edition, Elsevier Ltd.

Van Den Berge et al., "Clinical and inflammatory determinants of bronchial hyperresponsiveness in COPD", 2012, pp. 1098-1105, vol. 40, No. 5, European Respiratory Journal (8 pages).

Gosens et al., "Muscarinic receptor signaling in the pathophysiology of asthma and COPD", May 9, 2006, vol. 7, No. 73, Respiratory Research (15 pages).

Wine, Jeffrey J., "Parasympathetic Control of Airway Submucosal Glands: Central Reflexes and the Airway Intrinsic Nervous System", Apr. 30, 2007, pp. 35-54, vol. 133, No. 1, The International Society of Autonomic Neuroscience (32 pages).

\* cited by examiner

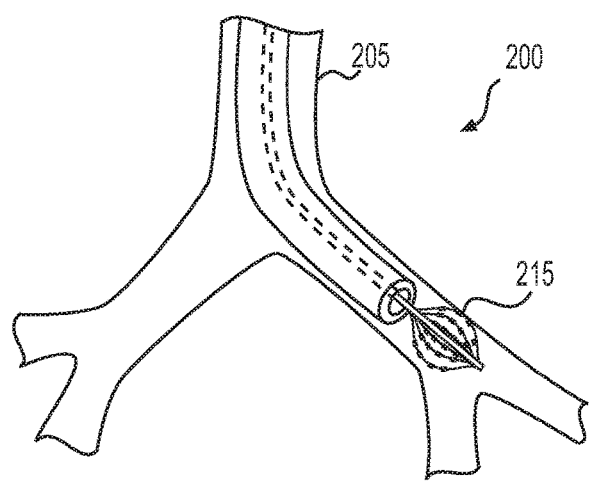
FIG. 2
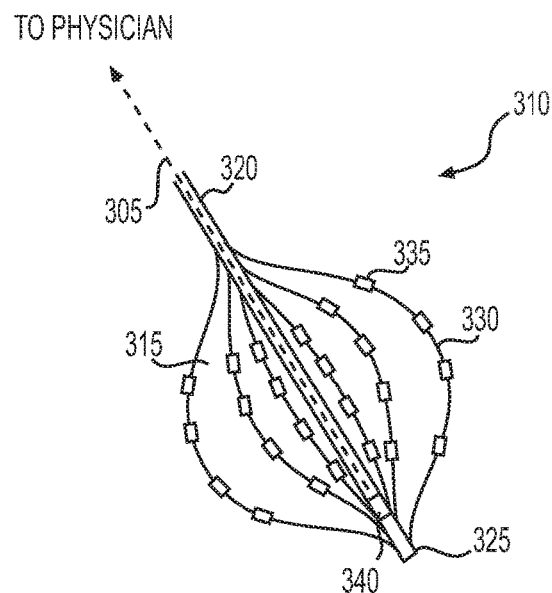
FIG. 3A
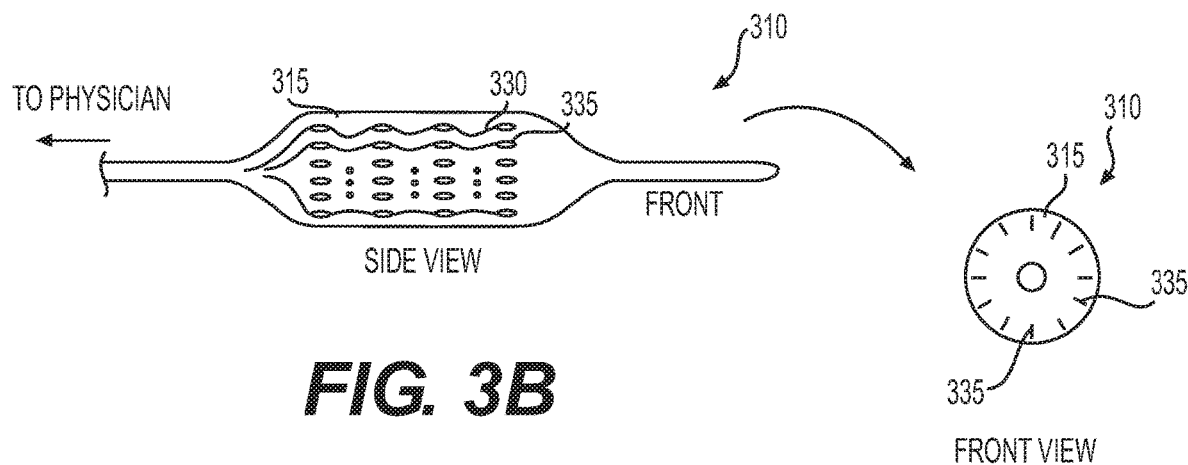
FIG. 3B
FIG. 3C
FIG. 3D

SYSTEMS AND METHODS FOR ASSESSING AND TREATING TISSUE

CROSS-REFERENCE TO RELATED APPLICATION

This patent application is a continuation of U.S. Nonprovisional patent application Ser. No. 14/658,676, filed on Mar. 16, 2015, now U.S. Pat. No. 9,974,597, issued May 22, 2018, which claims benefit of priority under 35 U.S.C. § 119 to U.S. Provisional Patent Application No. 61/955,449, filed Mar. 19, 2014, the entireties of which are incorporated herein by reference.

TECHNICAL FIELD

Various embodiments of the present disclosure relate generally to targeted treatment of tissue. More specifically, the present disclosure relates to devices, systems, and methods for assessing and identifying optimal locations for treatment, selective treatment at the identified optimal locations, and assessment of the effectiveness of the treatment.

BACKGROUND

Chronic obstructive pulmonary disease (COPD) includes conditions such as, e.g., chronic bronchitis and emphysema. COPD is estimated to affect about 64 million people worldwide, 15 million of which are in the United States alone, and is currently the third leading cause of death in the United States. The primary cause of COPD is inhalation of cigarette smoke, responsible for over 90% of COPD cases. The economic and social burden of the disease is substantial and is increasing.

Chronic bronchitis is characterized by chronic cough with sputum production. Due to airway inflammation, mucus hypersecretion, airway hyperresponsiveness, and eventual fibrosis of the airway walls, significant airflow and gas exchange limitations result. Emphysema is characterized by the destruction of the lung parenchyma. This destruction of the lung parenchyma leads to a loss of elastic recoil and tethering which maintains airway patency. Because bronchioles are not supported by cartilage like the larger airways, they have little intrinsic support and therefore are susceptible to collapse when destruction of tethering occurs, particularly during exhalation.

Acute exacerbations of COPD (AECOPD) often require emergency care and inpatient hospital care. AECOPDs are defined by a sudden worsening of symptoms (e.g. increase in or onset of cough, wheezing, and sputum changes) that typically last for several days, up to a couple weeks. Bacterial infection, viral infection, or pollutants typically trigger AECOPDs, which manifest quickly into airway inflammation, mucus hypersecretion, and bronchoconstriction, which cause significant airway restriction.

Despite relatively efficacious drugs (long-acting muscarinic antagonists, long-acting beta agonists, corticosteroids, and antibiotics) that treat COPD symptoms, a particular segment of patients known as "frequent exacerbators" often visit the emergency room and hospital with exacerbations and also have a more rapid decline in lung function, poorer quality of life, and greater mortality.

The autonomic nervous system provides constant control over airway smooth muscle, secretory cells, and vasculature, and therefore, some conventional methods have attempted to treat COPD symptoms by treating portions of the autonomic nervous system. For example, some conventional methods used to treat COPD include various anticholinergic drugs. Although sympathetic and parasympathetic branches of the autonomic nervous system innervate the airways, the parasympathetic branch dominates, especially with respect to control of airway smooth muscle and secretions. Cholinergic nerve fibers arise in the nucleus ambiguus in the brain stem and travel down the vagus nerve (right and left vagus nerves) and synapse in parasympathetic ganglia, which are located within the airway wall. These parasympathetic ganglia are most numerous in the trachea and mainstem bronchi, especially near the hilus and points of bifurcations, with fewer ganglia dispersed in distal airways. From these ganglia, short post-ganglionic fibers travel to airway smooth muscle and submucosal glands. Acetylcholine (ACh), the parasympathetic neurotransmitter, is released from post-ganglionic fibers and acts upon M1- and M3-receptors on smooth muscles and submucosal glands to cause bronchoconstriction and mucus secretion, respectively. Acetylcholine may additionally regulate airway inflammation and airway remodeling, and it may contribute significantly to the pathophysiology of obstructive airway diseases.

Wide varieties of stimuli (e.g., cigarette smoke, mechanical stimuli, and other irritants) are able to elicit reflex cholinergic bronchoconstriction through activation of sensory receptors in the larynx or airways. These sensory receptors primarily include rapidly adapting receptors (RARs) and C-Fibers, both of which have nerve endings in the epithelium. Activation of these afferent nerves causes a cholinergic reflex that is known to result in bronchoconstriction and an increase in airway mucus secretion through the activation of muscarinic receptors on airway smooth muscle cells and submucosal glands.

Bronchial hyperreactivity (BHR) may be present in a considerable number of COPD patients. Various reports have suggested BHR to be present in between ~60% and 94% of COPD patients. This "hyperreactivity" could be due to a "hyperreflexivity". However, there are several logical mechanisms by which parasympathetic drive may be overactivated in inflammatory disease. First, inflammation is commonly associated with overt activation and increases in excitability of vagal C-fibers in the airways that could increase reflex parasympathetic tone. Secondly, airway inflammation and inflammatory mediators have been found to increase synaptic efficacy and decrease action potential accommodation in bronchial parasympathetic ganglia; effects that would likely reduce their filtering function and lead to prolonged excitation. Thirdly, airway inflammation has also been found to inhibit muscarinic M2 receptor-mediated auto-inhibition of acetylcholine release from post-ganglionic nerve terminals. This would lead to a larger end-organ response (e.g., smooth muscle contraction) per a given amount of action potential discharge. Fourthly, airway inflammation has been associated with phenotypic changes in the parasympathetic nervous system that could affect the balance of cholinergic contractile versus non-adrenergic non-cholinergic (NANC) relaxant innervation of smooth muscle.

Because airway resistance varies inversely with the fourth power of the airway radius, BHR is believed to be a function of both bronchoconstriction and inflammation. Inflammation in the airway walls reduces the inner diameter (or radius) of the airway lumen, thus amplifying the effect of even baseline cholinergic tone.

Denervation and nerve stimulation therapies for the bronchial tree have been proposed to reduce bronchial hyperresponsiveness and the probability of AECOPD events. However, these denervation therapies are often non-selective in the region of the airway, either axially or radially, in where to treat to achieve the desired denervation effect. Rather, full circumferential coverage is often targeted in one or more locations throughout the airway in attempt to ensure the treatment region encompasses the targeted nerve(s). This may subject the patient to a greater risk of acute side effects such as inflammation and/or mucus production (and the associated airflow limitation associated with each) as well as other risks than may be required for effective denervation. Additionally, these existing therapies do not provide a real-time assessment of the efficacy of a treatment and thus do not provide patient customized therapy.

Accordingly, a need exists for selectively identifying optimal location for treatment of airway tissue and targeting nerves in the airway to optimize therapy location and to minimize unnecessary treatment to a patient's airway to minimize risk of short-term or long-term side effects.

SUMMARY OF THE DISCLOSURE

The present disclosure includes devices for treating tissue and related methods. In one aspect, the present disclosure is directed to a medical device. The medical device may include an elongate member, having a proximal end configured to be electrically coupled to an energy source, and a distal member disposed at a distal end of the elongate member. The distal member may include a plurality of contact elements configured to deliver stimulating energy to innervated tissue. The contact elements may also detect a response from the innervated tissue to the stimulating energy, and deliver therapeutic energy to the innervated tissue based on the response from the innervated tissue.

Various embodiments of the disclosure may include one or more of the following aspects: the distal member may be an expandable distal member, the plurality of contact elements may be positioned radially and axially along the expandable distal member, the plurality of contact elements may be arranged in a plurality of rows radially spaced about a longitudinal axis of the expandable distal member, each of the plurality of rows including contact elements that are longitudinally aligned in columns and each of the columns include contact elements that are radially spaced about the longitudinal axis at a same axial position, the contact elements may comprise portions configured to penetrate the innervated tissue, the contact elements of a row may be electrically connected in parallel, each of the plurality of contact elements may be separated by a non-energy delivering portion of the distal member, the device may further include a location detection member configured to transmit location information, the plurality of contact elements may be electrodes that deliver electrical energy, the contact elements may be electrodes and the therapeutic energy is ablative energy, the ablative energy may be sufficient to ablate the innervated tissue, the device may be coupled to a control unit and each of the contact of elements are configured to be independently controlled by the control unit, the distal member may have a shape selected from the group consisting of: a basket, a balloon, a spiral, and a loop.

In another aspect, the present disclosure is directed to a system for delivering energy to tissue including a user interface configured to display nerve stimulation response information and treatment information, and transmit user control instructions. The system also may include a control unit having a processor configured to receive the user control instructions and control energy output. In addition, the system may include an energy source coupled to the control unit, and a medical device. The medical device may include an elongate member having a proximal end electrically coupled to the energy source. The medical device also may include a distal member at a distal end of the elongate member. The distal member may include a plurality of contact elements configured to deliver stimulating energy to tissue, detect a response from the tissue to the stimulating energy, and deliver therapeutic energy and/or therapeutic substances to the tissue based on the response from the tissue.

Various embodiments may include the control system configured to control different modes of the system for delivering stimulating energy and delivering therapeutic energy, and the control system may be configured to change modes over time In another aspect, the present disclosure is directed to a method of treating innervated lung tissue. The method may include positioning a medical device at a target location, the medical device may include an expandable element and an array of contact elements, delivering stimulating energy to innervated tissue proximate the target location, and detecting responses from the innervated tissue to the stimulating energy. In addition, the method also may include determining one or more portions of the innervated tissue for therapy based on the responses detected from the innervated tissue to the stimulating energy, and delivering therapeutic energy and/or substances to the one or more portions of innervated tissue identified for therapy.

Various embodiments may include, during the step of delivering therapeutic energy, only the contact elements directed towards the one or more portions of innervated tissue determined for therapy deliver the therapeutic energy, sending locational information about the one or more portions of the innervated tissue to a user of the medical device, the step of determining comprises calculating energy profiles of the innervated tissue and comparing the energy profiles to identify the one or more of the portions of the innervated tissue having a minimum nerve activation threshold, the therapeutic energy is sufficient to treat the one or more portions of innervated tissue determined for therapy, a step of delivering stimulating energy to the one or more portions of innervated tissue to which the therapeutic energy was delivered after the step of delivering therapeutic energy, and the stimulating energy is delivered to the innervated tissue at a predetermined location, predetermined surface area, predetermined circumference, or a predetermined pattern.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

FIG. 2 is an in vivo perspective view of a distal portion of the medical device of FIG. 1 in an expanded configuration in accordance with another embodiment of the present disclosure.

FIGS. 3A, 3B, and 3C are partial perspective, side, and front, views, respectively, of a distal end of the medical device of FIG. 1 in an expanded configuration in accordance with an embodiment of the present disclosure.

FIG. 3D is a partial side view of the medical device of FIG. 1 in an expanded configuration with an embodiment of the present disclosure.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts. The present disclosure is directed to a medical device configured to deliver a stimulation to tissue, receive a response to the stimulation, process the response, determine a suitable type and location for delivering a therapy, selectively delivering the therapy based on the determination, evaluating the efficacy of the therapy, and, if necessary, repeating the stimulation and therapy.

Figure 1:
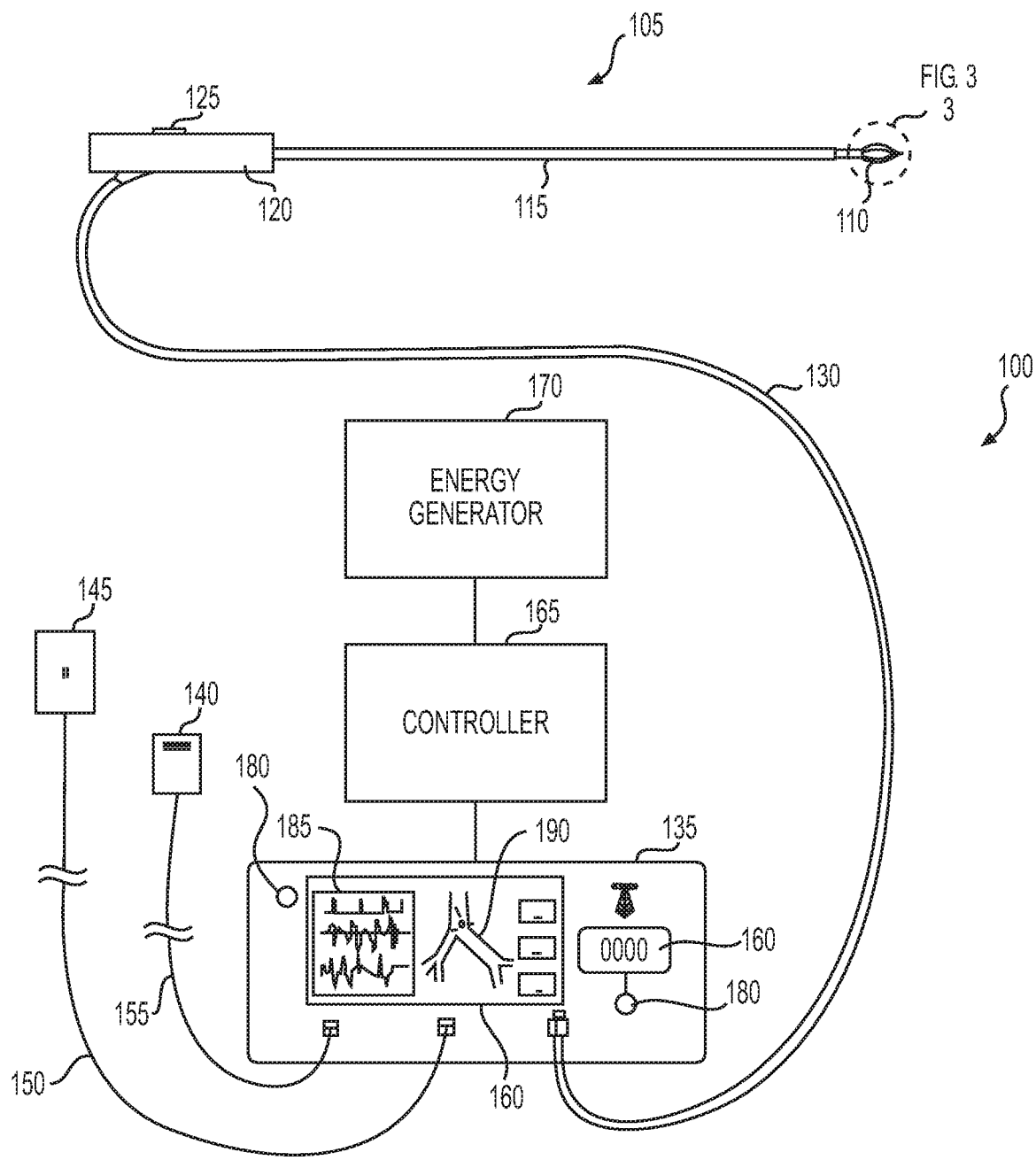
FIG. 1 is a schematic view of an exemplary system for delivering energy in accordance with an embodiment of the present disclosure.

A schematic view of an exemplary system 100 for transferring energy to tissue is illustrated in FIG. 1. The system 100 may include a medical device 105 having a distal end 110 configured for insertion into the body to transfer therapeutic energy and/or substances (e.g. cooling fluid, electrolytic fluid, etc.). The distal end 110 of the medical device 105 may be coupled to an elongate member 115 having a proximal end connected to a handle 120 for manipulation by a user, such as a physician or any other suitable medical professional.

The elongate member 115 may be configured and sized to permit passage through the working lumen of a commercially available bronchoscope, endoscope, or other suitable medical device, or over a guidewire. The device also may be advanced into the body with or without a steerable catheter, in a minimally invasive procedure or in an open surgical procedure, and with or without the guidance of various vision or imaging systems.

Portions of the handle 120 may be configured to be held or gripped by the user's hand. The handle 120 may include one or more selectors 125, such as a button, switch, knob, disc, lever, finger loop, etc., for manipulating (e.g. actuating, steering, expanding, retracting, activating, etc.) one or more portions and/or characteristics of the medical device 105 by the user's hand or fingers. The selector(s) 125 may be positioned on any suitable portion of the handle 120 in any suitable configuration, such as protruding from a surface of the handle 120 or in a recessed portion of the handle 120. The medical device 105 may be coupled to a user interface module 135 in any suitable manner to receive energy, and/or send and receive various signals. The coupling of the medical device 105 to the user interface 135 may be via a cable, such as a plurality of wires to transfer energy and signals, or the signals may be communicated wirelessly. For example, in the embodiment shown in FIG. 1, the handle 120 of the medical device 105 is coupled to the user interface module 135 via a cable 130 to receive energy generated by an energy generator 170 connected to a controller 165, which in turn may be connected to the user interface module 135.

The energy generator 170 may be any energy source, such as a battery or direct electrical current providing energy in a variety of forms, including microwave, cryogenic, thermal, laser, ultrasound, radio frequency (RF), etc. In some embodiments, the energy source may be replaced with or include a source of a therapeutic substance, such as a neurolytic agent, chemical ablation agent, etc. The controller 165 may be any computer or processing unit configured to modulate the amount of energy transferred to the medical device 105 per instructions received from the user interface module 135. The user interface module 135 may have various components including displays 160 for displaying information and receiving user input, and selectors 180 for receiving user input. The user interface module also may be connected to various other input components, such as a pedal 140, via various connectors. In some embodiments, the energy generator 170 may generate electrical energy in a monopolar manner, and the system 100 may include a return electrode 145 for attachment to a patient. Other embodiments may operate in a bipolar manner.

As further explained below, the distal end 110 of the medical device 105 may be expandable or capable of expanding, or include an element that is expandable or capable of expanding, and may include one or more contact elements configured to transfer energy and or receive and transmit diagnostic properties from the tissue at a target location in the body. The distal end 110 of the medical device 105 may be manufactured using any suitable materials in any suitable manner. For example, the distal end 110 may be manufactured using polymers, and/or metals (e.g. stainless steel, nitinol, etc.) having suitable properties such as elasticity, flexibility, shape memory, self-expansion, self-contraction, and/or rigidity. The distal end 110 also may have one or more coatings having suitable properties such as lubricious, drug eluting, and/or therapeutic properties. In addition, the surfaces of the distal end 110 may have one or more suitable features, such as roughened surfaces, protrusions, grooves, fenestrations, etc. The distal end 110 of the medical device may have any suitable size, shape, geometry, and/or other properties for insertion in the body for therapeutic use, such as tapered, widened, curved, looped, etc. portions. For example, the distal end 110 may have a curved surface configured to contact tissue on a curved portion of the body, such as the airway.

One or more portions of the distal end 110 may be formed of a radiopaque material so that they can be visualized under fluoroscopic guidance, or the distal end 110 of the medical device 105 may otherwise include radiopaque or other imaging markers for guidance. The markers may be used to ensure that a correct direction of therapy is applied.

The elongate member 115 may be removably or non-removably connected to the distal end 110 and may include a hollow lumen having one or more energy conducting components configured to transfer energy to the contact elements of the distal end 110 of the medical device 105. The hollow lumen of the elongate member 115 also may house conduits (e.g. wires, cables, transmitters, receivers) for receiving signals and/or data from the contact elements on the distal end 110. The elongate member 115 may be manufactured using any suitable materials, such as polymers, and metals, having suitable properties such as elasticity, flexibility, shape memory, rigidity. The elongate member 115 also may have one or more coatings, having suitable properties such as lubricious, drug eluting, and/or therapeutic properties. In addition, the surfaces of the elongate member 115 may have one or more suitable features, such as roughened surfaces, protrusions, grooves, fenestrations, etc. The elongate member 115 may be made of the same or different material(s) as the distal end 110. The elongate member 115 of the medical device may have any suitable size, shape, geometry, and/or other properties for insertion in the body for therapeutic use.

The elongate member 115 may be formed to have, or may be removably or non-removably coupled to a handle 120. The handle 120 may house the same conduits (e.g. wires, cables, transmitters) as the elongate member 115 for receiving signals and/or data from the distal end 110 or may have different conduits with connections configured to couple to the ends of the conduits in the elongate member 115. The handle 120 may be manufactured using any suitable materials, such as plastics, polymers, and metals, having suitable properties such as rigidity and flexibility, etc., and may include one or more steerable and/or non-steerable portions. The handle 120 may be made of the same or different material(s) as the elongate member 115 and/or the distal end 110 and may have one or more coatings, such as antibacterial coatings. The surface of the handle 120 may be roughened, textured, etc., to aide in being held or gripped by a user. The handle 120 may have any suitable size, shape, geometry, and/or other properties for use by the user.

The cable 130 connecting the medical device 105 and the user interface 135 may include an insulating cover manufactured in any suitable manner, e.g. rubber, polymer etc., and one or more lumens, and may house one or more conduits. The cable 130 may transfer energy, such as electrical (monopolar or bipolar) or any other suitable energy to and from the medical device 105 and the energy generator 170 and also may transfer various signals, for example, audio, visual, geophysical, electrical, magnetic, etc. The conduits in the cable 130 may be manufactured using any suitable material, such as metals and may haven any suitable size, shape, and geometry. The ends of the cable 130 may be coupled to the medical device 105 and the user interface module 135 in any suitable manner.

The user interface module 135 may include one or more displays 160 (e.g. digital, LED, LCD, plasma, etc.) and/or selectors 180. One or more of the displays 160 may be a touch screen configured to receive input from a user, and may display various information, such as diagnostic data received from the contact elements on the distal end 110 of the medical device 105, such as temperatures, electrical stimulation response data, etc. For example, the user may input various parameters such as pace (e.g. current, voltage, and frequency), time, duration, type, amount, coverage area, and/or other characteristics of stimulating and therapeutic energy or treatment via the user interface module 135. The display(s) 160 may also show the location of the medical device 105 and its various components in the body, e.g. via a one-dimensional or multi-dimensional map based on signals received from the contact elements. The user interface module 135 also may be configured to receive and process various programs and instructions and save the data in memory and send data to other devices and entities.

The user interface module may include a data communication interface for packet data communication and a central processing unit (CPU), in the form of one or more processors, for executing program instructions, such as programs for analyzing diagnostic data received by the medical device 105. The user interface module 135 also may include an internal communication bus, program storage, and data storage for various data files to be processed and/or communicated by the user interface module 135 such as ROM and RAM, although the user interface module 135 also may receive programming and data via network communications. The hardware elements, operating systems, and programming languages of the user interface module 135 may be conventional in nature, and it is presumed that those skilled in the art are adequately familiar therewith. The user interface module 135 also may include input and output ports to connect with input and output devices such as keyboards, mice, touchscreens, monitors, displays, etc. Of course, the various functions may be implemented in a distributed fashion on a number of similar platforms, to distribute the processing load.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of a communication network into the computer platform of a server and/or from a server to the user interface module 135. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

In one embodiment, as shown in FIG. 1, the user interface module 135 may be connected to a controller 165 configured to modulate energy generated by the energy generator 170. In many variations of the system 100, the controller 165 may include a processor having similar characteristics as the processor described above in reference to the processor of the user interface module 135. The processor of the controller 165 may be generally configured to accept information from the system 100, and process the information according to various algorithms to produce control signals for controlling the energy generator 170. The processor of the controller 165 also may accept information from other components of the system 100, such as the user interface module 135. The processor may process the information according to various algorithms and produce information signals that may be directed to the display(s) 160 of the user interface 135. The information signals may inform the user of the system status, component status, procedure status, medical device location, treatment status, stimulus response, or any other useful information that is being monitored by the system 100.

For example, the user interface module 135 may receive instructions from the user or automatically via a program, to transfer stimulating energy (e.g. a stimulating mode) to the target location or transfer therapeutic energy (e.g. a therapeutic mode) such as energy sufficient to treat tissue.

FIG. 2 illustrates an in vivo perspective view of a distal portion 210 of the medical device 105 of FIG. 1 in an expanded configuration in an airway, although the medical device may be used in any suitable portion of the body. The distal end 210 of the medical device may be expanded so that external surfaces of the distal end 210 may contact portions of tissue at a target location 215, transfer energy, and receive diagnostic information from the tissue.

FIGS. 3A, 3B, 3C, and 3D show various views of a distal end 310 of a medical device, for example, the medical device 105 shown in FIG. 1. The distal end 310 may include a central axis 305, an expandable member 315, portions of which may be connected to a central tubular member 320 coaxial with the central axis 305, and having a distal tip 325. In one embodiment, the expandable member 315 may be an inflatable balloon, the surface of which may include a plurality of rib members 330 extending axially from a proximal end of the expandable member 315 to a distal portion of the expandable member 315. In another embodiment, the expandable member 315 may comprise a plurality of expandable rib members 330 the ends of which may be connected to portions of the tubular member 320, allowing air, and/or blood to flow between the rib members 330.

As shown in FIGS. 3A-3C, each rib member 330 may include a plurality of contact elements 335 configured to transfer energy to tissue (e.g. act as electrodes), receive diagnostic information from tissue (e.g. act as sensors), send the received diagnostic information for processing, and/or perform locating functions. The rib members 330 may be coupled directly or indirectly to the energy generator 170 via various energy conducting components shown in FIG. 1. As shown in FIGS. 3A-3C, each rib member 330 may be evenly radially spaced around the expandable member 315 and each contact element 335 on each rib member 330 may be evenly spaced axially along the rib members 330 to form columns and rows. In the example shown, the distal end 310 includes twelve rib members (see FIG. 3C), each having four or more, or at least five contact elements 335. As shown in FIG. 3C, the expandable member has contact elements (e.g. electrodes) arranged in a grid pattern of columns and rows. In other embodiments, the rib members 330 and the contacts elements 335 may have any other suitable arrangement. The rib members 330 may be configured to supply energy to the contact elements 335 based on instructions from the user interface module 135, which selectively control which rib member(s) 330 should receive energy, to the controller 165, as well as the type, amount, duration, frequency, and any other properties of the energy.

In addition, the user interface 135 and controller 165 may control the transmission and the activation of various modes of the contact elements 335 via the rib members 300 connected to the contact elements 335. For example, the user interface module 135 and controller 165 may only provide stimulating energy to one of the plurality of the rib members 330, or more discretely, only to a portion of a single rib member 330, so that only a portion of the plurality of contact elements 335 deliver stimulating energy to the tissue and in turn only a selected portion of tissue is stimulated. Similarly, the user interface module 135 and controller 165 may only provide therapeutic energy to a portion of the rib members 330, (e.g. alternately adjacent rib members 330) so that only a portion of the contact elements 335 deliver therapeutic energy and in turn only a selected portion of tissue receives energy.

For example, in a tubular shaped target location (e.g. the airway), the user interface module 135 may only supply therapeutic type energy to selective rib members 330 connected to selective contact elements 335 in contact with a particular segment/arc of the airway tissue identified for treatment, so that only that segment/arc of the airway tissue receives the therapeutic energy and other portions do not. In this manner, the medical device may achieve treatment of an axial or circumferential portion of airway tissue, while not damaging tissue not identified for treatment.

The expandable member 315 may be manufactured using any suitable materials, such as polymers and metals having any suitable combination of properties such as elasticity, flexibility, shape memory, self-expanding, self-contracting, and/or rigidity, and may have one or more coatings, such as lubricious, drug eluting, therapeutic, etc. The expandable member 315 may have any suitable size, shape, geometry, and/or other properties for insertion in the body for therapeutic and/or diagnostic use and may expand in any suitable manner, such as via insufflation fluid and/or gas, response by a shape memory material to a stimulus, shape memory material bias (e.g. self-expansion), and/or any other suitable manner. For example, as shown in FIG. 3D, the expandable member 315 may include raised and recessed portions configured to allow air to flow during placement in an airway.

The amount, type, and other expansion and retraction properties may be automatically controlled by the user interface module 135 and controller 165, for example, in response to any diagnostic or locational information received from the distal end of the medical device.

The tubular member 320 and the rib members 330 may be manufactured using any suitable material(s) configured to conduct and transfer energy, such as metals and may use the same or different materials. Examples of suitable tubular member 320 materials may include polymer materials such as PTFE, ETFE, Polyurethane, or any other insulative material. The tubular members 320 rib members 330 may have any suitable size, shape, geometry, and/or other properties for insertion in the body for therapeutic and/or diagnostic use.

The contact elements 335 may be manufactured using any suitable material(s) configured to conduct and transfer energy and send and receive diagnostic information, such as metals. The contact elements 335 may have any suitable size, shape, geometry, and/or other properties for insertion in the body for therapeutic use. The contacts 335 may be an electrode, a printed electrode, a basket electrode, a resistive heating element, cyroprobe, etc., configured to delivery energy to tissue and configured to include a sensor component, which may be configured to receive diagnostic information from the tissue, and/or a microwave antenna. The contact elements 335 may include a lens, curved transducer, phased array (e.g., linear phased array, curvilinear phased array, or convex sector phased array), or a combination thereof, configured to focus the energy into a small focal zone. In one embodiment, each contact element 335 may further be divided into smaller increments, for use in selectively applying energy to and receiving diagnostic information from, smaller portions of tissue.

In some embodiments, the contact elements 335 may be configured to transfer therapeutic and stimulating energy, receive and transmit diagnostic information, transmit location information, and perform imaging, mapping and navigation functions, etc. For example, the contact elements 335 may include a GPS-like sensor (e.g. using impedance, magnetic, or any other technology used for mapping). The location and other data from the contact elements 335 may be used by mapping software, e.g. stored and executed by the user interface module 135 and controller 165, to generate a map, such as a multi-dimensional map of the nerve traffic and/or muscle activation times in and around the airways, or tissue around other suitable locations. In some embodiments, the contact elements 335 may be configured to map the interior of the airway and provide signals to generate a 3D image of the airway.

The contact elements 335 may be configured for energy delivery around a larger circumference of the airway, or other lumen such as the esophagus, and be directed at additional locations other than innervated tissue. In some embodiments, contact elements 335 may be directed toward smooth muscle tissue in the airways to achieve reduced bronchoconstriction, reduced airway resistance, improved air flow, etc., (by e.g., inhibiting or reducing smooth muscle function). In some embodiments, contact elements 335 may be directed toward body tissues affecting other diseases such as, e.g., asthma, asthma attacks, etc. where bronchoconstriction, mucus hypersecretion, and cough are also observed, chronic cough, chronic bronchitis, and cystic fibrosis.

The sensor components of the contact elements 335 may include electrical stimulation sensor and/or temperature sensors configured to detect a presence/amount of therapy delivered. In another embodiment, the sensors may include Doppler ultrasound sensors to detect blood vessels via, e.g., Doppler ultrasound. In some embodiments, the sensors may detect impedance. In another embodiment, the sensors of the contact elements 335 may sense electrical measurement of nerve traffic and/or muscle activation signals that corresponds to an efficacy of the treatment. In another embodiment, the sensors of the contact elements 335 may include a vision system for direct observation. In yet another embodiment, the sensors of the contact elements 335 may include a force transducer to measure radial force in the airway. In some embodiments, the sensors of the contact elements 335 may include strain gauge technology, such as fiber Bragg grating (FBG) fibers and may include a pressure sensor.

The contact elements 335 may deliver energy in any suitable manner. For example, energy may be applied for any suitable period of time (e.g. 0.1 to 600 seconds), any suitable tissue temperature (e.g. 40° C. to 95° C.), at any suitable frequency (e.g. RF energy between 10 MHz to 1000 MHz and/or microwave energy between 1000 MHz to 2000 MHz), and at any suitable power (e.g. 0.01 Watts to 100 Watts).

Figure 4:
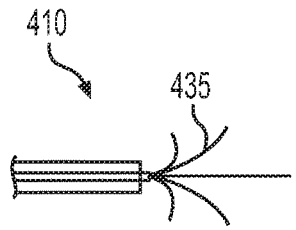
FIG. 4 is a partial side view of a distal end of a medical device in an expanded configuration in accordance with another embodiment of the present disclosure.

FIGS. 4-9 show various distal ends 410, 510, 610, 710, 810, and 910 of other embodiments of medical devices in accordance with the present disclosure and are similar in some respects to the expandable member 310 described above and shown in FIGS. 3A-3C. Some of the distal ends shown in FIGS. 4-9 may be configured to self-expand, include portions for penetrating tissue, have atraumatic portions, and include sensor components. As shown in FIG. 4, the distal end 410 includes a plurality of elongate contact elements 435 configured to radially extend from the elongate member 115 of the medical device 105. Each of the elongate contact elements 435 may be configured to be selectively controlled to transfer energy and/or transmit signals.

Figure 5:
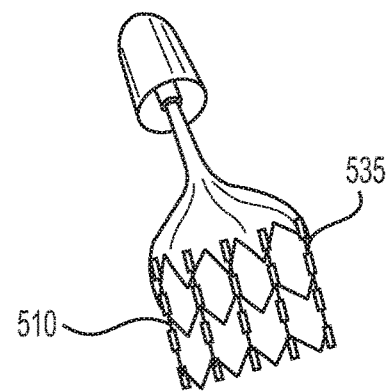
FIG. 5 is a partial side view of a distal end of a medical device in an expanded configuration in accordance with another embodiment of the present disclosure.

FIG. 5 shows a distal end 510 of the medical device 105 having an expandable stent configuration of contact elements 535 without an inflatable member. Each contact element 535 may be configured to be selectively controlled to transfer energy, and/or transmit signals.

Figure 6:
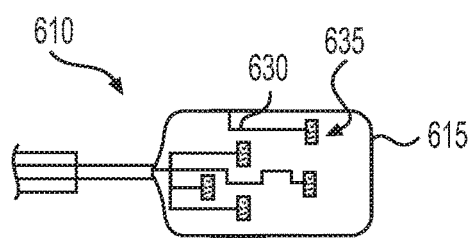
FIG. 6 is a partial side view of a distal end of a medical device in an expanded configuration in accordance with another embodiment of the present disclosure.

FIG. 6 shows a distal end 610 having an expandable member 615, such as a balloon. Each rib member 630 may be disposed on a surface of the expandable member 615. The rib members 630 may have different lengths and shaped so that contact elements 635 are arranged in a non-uniform pattern. The rib members 630 may be metal foil or the like that is deposited on a balloon surface and is flexible and has the ability to expand. Each rib member 630 can be selectively controlled to transfer energy, and/or transmit signals from the contact elements 635.

Figure 7:
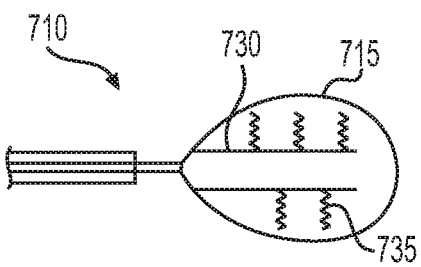
FIG. 7 is a partial side view of a distal end of a medical device in an expanded configuration in accordance with another embodiment of the present disclosure.

FIG. 7 shows another distal end 710 having an expandable member 715, such as a balloon and rib members 730 disposed on a surface of the expandable member 715. Rib members 730 have different lengths and include contact elements 735 at the ends of the rib members 730. Contact elements 735 have a zigzag shape. Each rib member 730 may be configured be selectively controlled to transfer energy, and/or transmit signals. The rib members 730 may be metal foil or the like that is deposited on the balloon surface. The contact elements and/or the rib members 730 may be flexible and have the ability to expand as the balloon expands.

Figure 8A:
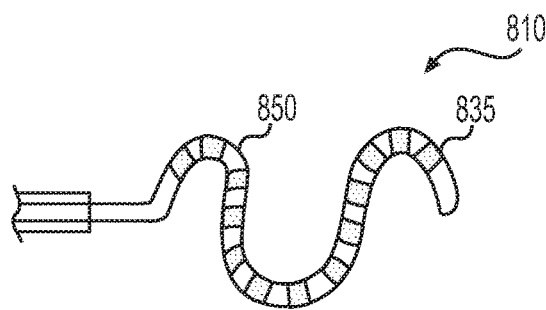
FIG. 8A is a partial side view of a distal end of a medical device in an expanded configuration in accordance with another embodiment of the present disclosure.
Figure 8B:
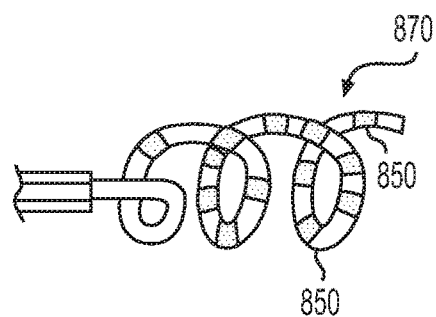
FIG. 8B is a partial side view of a distal end of a medical device in an expanded configuration in accordance with another embodiment of the present disclosure.

FIG. 8A shows a distal end 810 having a curved lead member 850, and contact elements 835 evenly spaced along the surface of the lead member 850. The lead member 850 may have a sinusoidal shape and may be configured to self-expand when released from the elongated member 115. FIG. 8B shows a distal end 910 having a spiral or loop shaped lead member 950, and contact elements 935 evenly disposed along the surface of the lead member 950. The lead member 950 may have a sinusoidal shape and may be configured to self-expand when released from the elongated member 115.

Figure 9:
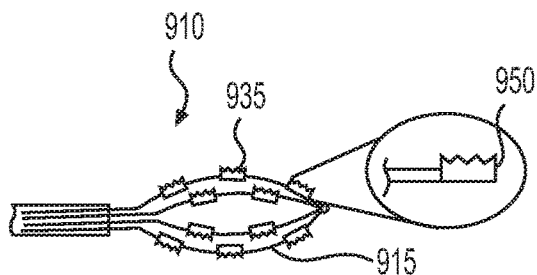
FIG. 9 is a partial side view of a distal end of a medical device in an expanded configuration in accordance with another embodiment of the present disclosure.

FIG. 9 shows a distal end 910 of the medical device 105 having an expandable basket configuration of contact elements 935 without an inflatable member. Each contact element 935 may be selectively controlled to transfer energy, and/or transmit signals. Each contact element 935 may comprise one or more protrusions 950, such as barbs, configured to penetrate tissue, such as airway wall tissue at any suitable depth so as to anchor or retain the distal end 910 of the medical device at a location.

In some embodiments, the contact elements 935 may include various fixation components to temporarily stabilize the distal end 910 relative to the adjacent tissue during the sensing/intervention process. Examples of such fixation components may include air channels configured to apply negative pressure/suction to adhere to the tissue, textured surfaces that create mechanical friction with the adjacent tissue, extendable/retractable helices or hooks, etc.

In the embodiments shown in FIGS. 4-9, portions of the distal end, such as the contact elements, may each make contact with an epithelial surface, or may be configured to pierce through an epithelial surface. In piercing through the epithelial layer, portions of the distal end may reside within the tissue space of the airway wall or reside on the basal surface of the airway. This may provide better proximity of the contact elements to the innervated tissues.

Figure 10:
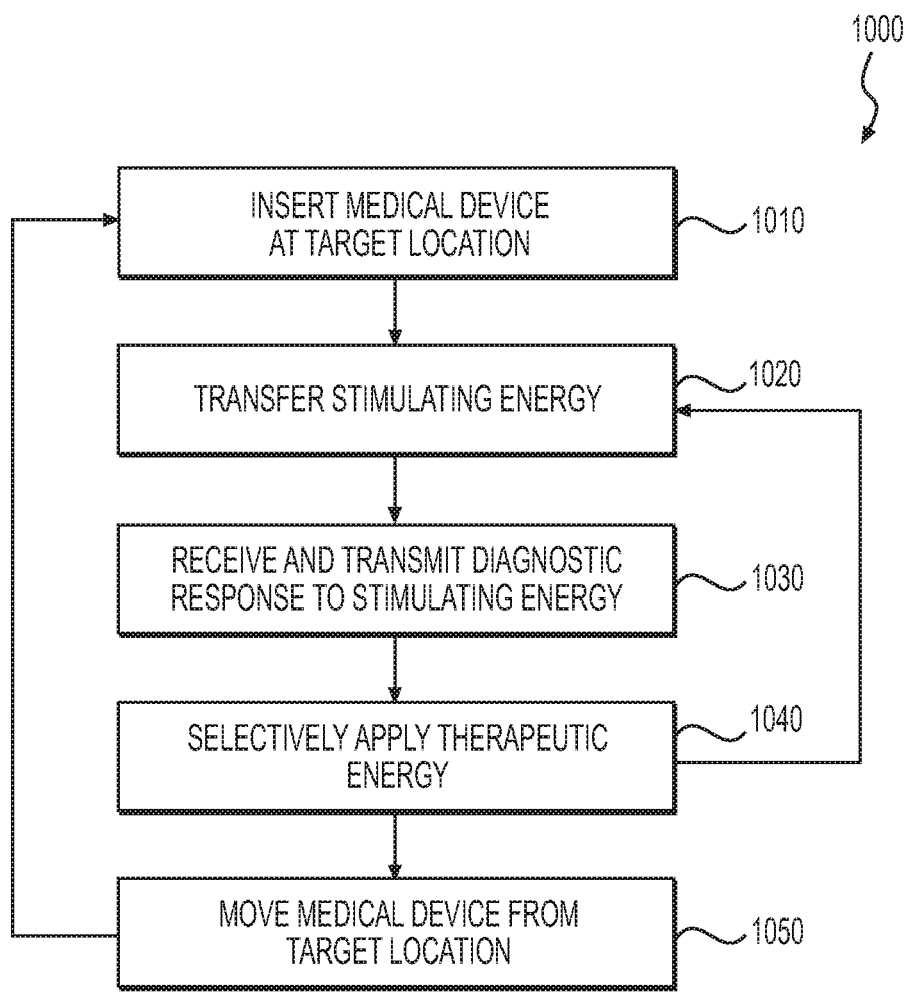
FIG. 10 is a flow diagram of a method for treating tissue in accordance with an embodiment of the present disclosure.

FIG. 10 shows a flow diagram of a method 1000 for treating tissue in accordance with an embodiment of the present disclosure. The method may be used for treating any suitable disease, such as diseases of the airway discussed above. At step 1010, a portion of a medical device, such as medical device 105 shown in FIG. 1, may be inserted into location near a target tissue. The location may be any portion of the body, such as a portion of the airway. The target tissue may be any type of tissue, such as nerve, or muscle tissue. In some embodiments, the target tissue may be a portion of a nerve, while in other embodiments, the target may include the entirety of a nerve. In some embodiments, a location of the nerve(s) to be targeted may be determined by direct visualization, of, e.g., an anatomical structure, by scanning/imaging, or by any other suitable means.

The medical device may be inserted in any suitable manner, such as using, e.g., an endoscope, bronchoscope, guide catheter, steerable catheter, etc. A plurality of channels may be disposed through the endoscope or bronchoscope member to allow for a variety of tools to be passed through. The medical device may be manipulated, for example expanded, or adjusted so that a distal end of the medical device may contact portions of tissue at the location. The location of the distal end of the medical device may be transmitted via a transmitter, for example, for display as a 3D image of the target location.

At step 1020, the medical device may transfer stimulating energy to tissue portions at the location. The medical device may transfer or deliver energy by contacting portions of the tissue with portions of the contact elements or by being in close proximity to the portions of the tissue. The stimulating energy may be any suitable type or combination of types, such as electrical, radio frequency (RF), microwave, laser, thermal (heating or cooling), acoustic or sonic energy, such as, e.g., high-intensity focused ultrasound (HIFU), delivery of a neurolytic agent, delivery of an anticholinergic drug, or any other energy. The transfer of the stimulating energy by the medical device may only be by a portion of the contact elements, such as one or more rows of contact elements.

In one embodiment, the stimulating energy may be automatically transferred/delivered in pulses at a predetermined pace and/or for a predetermined time. For example, the stimulating energy may be delivered every 10 milliseconds for a total duration of one seconds or any other suitable time increment. The same amount and pace of stimulating energy may be delivered by each row of contact elements in turn. Once all the rows have completed a round of delivering the same amount and pace of stimulating energy, a new round may commence in which the amount and/or pace of stimulating energy is automatically incrementally increased or decreased relative to the previous round. This cycle of stimulating energy delivery by each row of contact elements may be automatically repeated until a maximum or minimum energy amount is reached.

In another embodiment the pace, time, duration, type, and/or other characteristics of the stimulating energy may be inputted by the user via the user interface module 135 and/or controller 165.

At step 1030, the medical device may receive and transmit diagnostic responses to the stimulating energy. This step of receiving and transmitting diagnostic responses to the stimulating energy transferred in step 1020 may be performed by a portion of the contact elements, for example, those rows which did not transfer the stimulating energy. The step of transmitting diagnostic responses to the stimulating energy may occur simultaneously with the step of transferring stimulating energy and/or a discrete period following the stimulating energy delivery. The diagnostic responses may be any suitable response and may be transmitted via the contact elements to a processor, such as a processor in the user interface module, controller, or any other processor, via a conduit connected to the medical device or via electronic signals (e.g. wireless communication over a network, BLUETOOTH, near field communication, radio frequency, etc.)

Based on the received diagnostic responses from each row of contact elements at each increment of stimulating energy, the processor may generate a response location profile of the tissue at the target location. The response location profile may identify which portions of the tissue exhibited the lowest threshold to the stimulating energy. These portions of tissue may be further identified as requiring treatment, such as ablation.

In some embodiments, where the nerve may be pre-ganglionic parasympathetic nerve(s) (nerve trunks), a therapeutic treatment may encompass a number of treatments (e.g., fewer than five) in each mainstem or first generation bronchus, or second generation bronchus of a short treatment length each (e.g. less than one cm). In other embodiments where the nerve is a sensory nerve fiber(s), ganglia, or post-ganglionic parasympathetic nerve(s), a treatment may encompass substantially more treatments (and/or a larger area per treatment) to achieve a desired effect. In other embodiments, a therapeutic treatment may encompass treating smooth muscle, for example in a plurality of airway generations (e.g. between generations 2 and 6).

At step 1040, the medical device may selectively apply therapeutic energy to one or more tissue portions identified for receiving therapeutic treatment. In one embodiment, the therapeutic energy may be the same type of energy as the stimulating energy, but may be greater (e.g. double or triple) in intensity. In another embodiment, the stimulating and therapeutic energy may be of different types (e.g. electrical and laser). For example, the processor may determine, based on the diagnostic response data received at step 1030, that only a portion of tissue having a specific size and location should receive therapeutic energy treatment, such as ablating energy. In the case of RF ablation, for example, if the user would like to treat only a nerve trunk, electrodes in the 90-degree radial "window" around the nerve could be activated to deliver treatment, leaving the other 270-degrees of airway non-treated, for example. This may significantly reduce the amount of tissue that is affected by the ablation therapy and therefore reduces the likelihood of adverse events due to inflammation and acute mucus production. The processor may send instructions to the medical device to deliver therapeutic energy from a certain contact element, portions of a contact element, or one or more columns, rows, or various groups of contact elements, which are in corresponding contact with the portions of tissue identified for receiving therapeutic therapy. In this manner, only the portions of the tissue identified for receiving therapeutic energy receive the therapy, while other portions of tissue do not.

Steps 1020 and 1030 may be repeated to evaluate if the therapeutic step 1040 was effective. For example, the contact elements in contact with the tissue that received the therapeutic energy may be switched to transfer stimulating energy and receiving and transmitting diagnostic response data to determine if the therapeutic treatment energy was effective by generating a response location profile of the tissue at the target location. The response location profile may identify which portions of the tissue exhibited the lowest threshold to the stimulating energy. If the treated tissue is identified as still eliciting any or an undesired level of response to the stimulating energy, this may indicate that the previous treatment step 1040 was not yet effective. In this case, the treatment step 1040 may be repeated at the same, less, or greater level than the original therapeutic treatment energy along with steps 1020 and 1030 until the identified tissue no longer elicits a response.

At step 1050, once it is determined that the tissue identified for treatment has been successfully treated (e.g. the identified tissue no longer elicits a response to the stimulating energy) the medical device may be moved from the target location to another target location and the method repeated. In some embodiments, the method may be completed in a single treatment (e.g., one patient visit), though in other embodiments, the therapy may be completed in multiple treatments (e.g., in multiple patient visits).

Example

The distal end of the medical device has a configuration as shown in FIGS. 3A-3C. Specifically, an expandable member has 48 contact elements (e.g. electrodes) arranged in a pattern of rows and columns. The expandable member has twelve rows arranged longitudinally, each row having four contact elements (e.g. electrodes). The expandable member has four rows arranged circumferentially, each row having twelve contact elements (e.g. electrodes). Each contact elements (e.g. electrodes) is spaced approximately 30 degrees apart for its circumferentially adjacent neighboring contact element (e.g. electrode). Each of the contact elements (e.g. electrodes) arranged longitudinally may be connected to each other in parallel via an electrically conductive rib member. The electrically conductive rib member is in turn coupled to an electrical voltage source via a user interface module and or controller and supplies current to the electrodes. The distal end of the medical device is positioned into a bronchus and expanded.

Following positioning and expansion of the distal end, an impedance measurement is performed by the sensor portions of the electrodes and transmitted to the processor, either in the user interface module or the controller, to calculate the impedance between all neighboring rows of electrodes (e.g. between rows 1 and 2, between rows 2 and 3, etc.) The impedance value will provide information of which rows are making best contact with the bronchi tissue and thus allowing the user to select which rows to use for testing. The impedance values are stored as the locational impedance in memory for later use in calculating a minimum activation voltage for activating a portion of tissue.

A profile curve is then generated to identify locations of muscles and nerves for treatment. The profile curve will identify those portions of tissue that exhibit the lowest threshold to electrical current. To identify this tissue, an amplitude comparison may be made amongst the different electrode locations and the location with the highest amplitude response at the lowest current value may be identified as a potential target for treatment. The profile curve is generated by delivering cycles of stimulating electrical charge from each row of electrodes. The amplitude and/or pace of the stimulating electrical current are incrementally increased in each cycle.

Specifically, a stimulating electrical pulse is applied from each row of electrodes during an initial cycle starting at a suitable current, such as 1 mA and incrementally increasing, for example by 1 mA up to a maximum current, for example of 10 mA. Any suitable number of pulses, such as 20 pulses, could be delivered at each current value for each electrode pair at any suitable frequency e.g. 20 Hz or similar. The responses of the pulses may be averaged to obtain a consistent response. The stimulating pulse has a charge-balanced wave-form, such as biphasic rectangular, cathodic first waveforms of e.g. 100-500 us pulse-width. Each of the twelve rows of electrodes applies the same stimulating electrical pulse in turn.

While two electrodes in a row are selected for stimulation in bipolar mode, the remaining electrodes in that row can be used to record the response as well as the remaining electrodes on the adjacent rows in response to the stimulating electrical pulse. Specifically, the two rows adjacent to each side of the active row detect electromyography (EMG) and electroneurography (ENG) responses to the stimulating electrical pulse. EMG evaluates the electrical activity produced by muscles, and ENG evaluates the electrical activity produced by nerves.

The rows not adjacent to the active row may also detect EMG and ENG responses or may be idle (e.g. in a non-stimulating and non-detecting mode). EMG and ENG responses are acquired at discrete time intervals, such as about 1 to 20 milliseconds following the delivery of the stimulating electrical pulse. The detection of the EMG and ENG responses by the non-active rows may also include a stimulation artifact, which is an artifact due to saturation of the non-active rows. However, this response may be eliminated via use of various software. Recording may be done for all electrodes in tripolar mode where the signal amplified is formed by subtracting the signal recorded from any electrode from its adjacent electrodes within the same row.

Immediately or soon after the active row has completed applying the stimulating electrical pulse, it also detects EMG and ENG responses. However, this response detection may not include the stimulation artifact, as the detection does not occur while the active row is applying the stimulating electrical pulse. The detected EMG and ENG responses are sent to the processor for processing.

Once a round of the stimulating electrical pulse has been completed, a next round commences having an incrementally higher current or voltage value or temporal value and the responses are detected in the same manner as described above. The increments of the pulse amplitudes are at 1 mA up to 10 mA in increments of 1 mA. The increments of the pulse rates may be about 20 times per second. The cycles of stimulating electrical pulse continue until a maximum electrical current (e.g. 10 mA) is reached or the signals recorded are sufficient to locate a treatment target.

Figure 11:
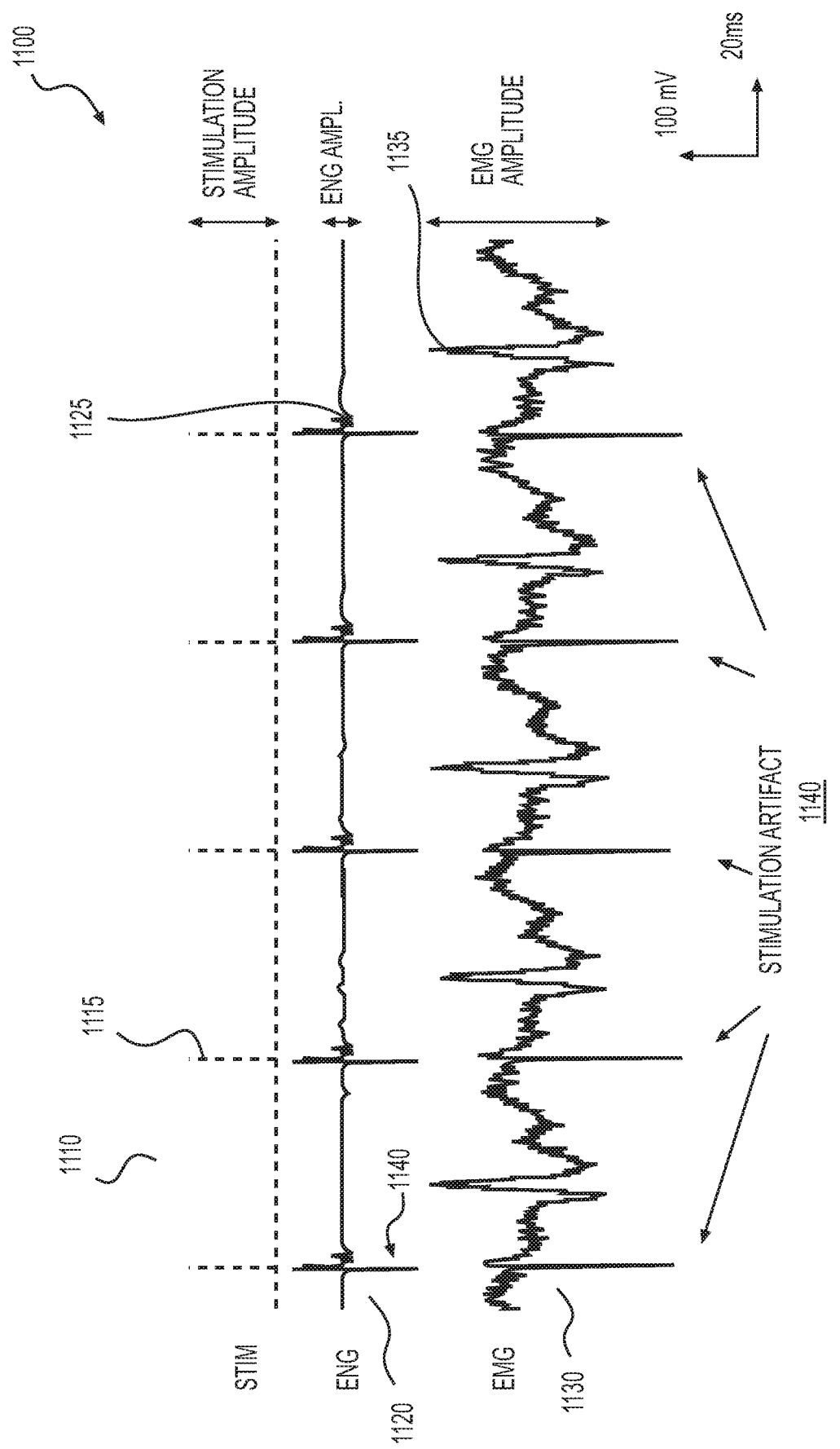
FIG. 11 shows stimulating pulse and response graphs.

FIG. 11 shows graphs 1100 of a stimulating electrical pulse 1110 and ENG 1120 and EMG 1130 responses. The stimulating electrical pulse has uniform amplitude of 100 mV at a uniform rate. The ENG 1120 and EMG 1130 responses to each of pulse each have an artifact 1140 due to the electrical stimulus. The ENG 1120 and EMG 1130 graphs each show a peak 1125 and 1135 associated with each pulse. Following a completion of all the rounds of stimulating electrical pulses, the processor processes the EMG and ENG response data to generate the profile curve identifying portions of muscle and nerves having the lowest threshold for electrical charge (e.g. are activated with the lowest electrical charge). These portions are identified for ablation treatment. The processor may be in the user interface module or controller.

This activation threshold is calculated as the minimum current between two rows of electrodes that elicits a clear EMG response. This current may then be divided by the locational impedance to result in a voltage, which indicates a voltage profile around the rows of electrodes where the minimum nerve activation voltage able to elicit a muscle contraction is located. In situations where more than one local minimum voltage is found, two potential nerve locations may be identified.

Therapeutic energy is then initiated between the rows of electrodes that indicated the smallest local minimum voltage(s). In this way, only the tissue in the vicinity of the nerve(s) is treated.

Following treatment, the process of creating a profile curve by applying stimulating electrical pulses is repeated with a voltage value double the previously determined activation threshold in order to confirm that the therapy was successful. In this way, it is determined if the treatment was effective or if the treated tissue is still eliciting a response. A doubling of the minimally necessary voltage to elicit an EMG response may indicate that all neural tissue in the close proximity to the distal end of the medical device has been altered.

In yet another example, devices of the present disclosure may be used to identify optimal locations for stimulation and/or treatment. Those identified optimal locations then may be treated using the devices. Once a treatment therapy has been completed, the device may be left in place at the treatment location, and the airway may be stimulated proximally to determine whether the treatment was successful using the different contact points on, e.g., the expandable mesh.

Alternatively, after the treatment therapy has been completed, the device may be retracted, and an activation response may be measured from a retrograde activation proximal to the treatment location. The device then may be advanced distally beyond the treatment location and stimulated to measure an activation response from an otograde activation. The activation response from the retrograde activation may be compared to the activation response measured from the otograde activation. The comparison of these activation responses may differ after a successful treatment as compared to an unsuccessful treatment. For example, after a successful treatment, only stimulation distally to the treatment location may provide a relatively large EMG response. However, after an unsuccessful treatment, both stimulation proximally and distally may provide relatively equal and large EMG responses. These mechanisms may allow for a practitioner to determine whether a treatment was successful, reduce treatment procedure times, reduce energy used, reduce healing time, and provide for a treatment with fewer complications.

The present disclosure achieves selective identification and targeting of nerves to optimize therapy location and minimizes unnecessary treatment of unaffected tissue to minimize risk of short-term or long-term side effects. This additionally may achieve a reduction in procedure time by significantly reducing the number of treatment regions required.

Any aspect set forth in any embodiment may be used with any other embodiment set forth herein. The devices and apparatus set forth herein may be used in any suitable medical procedure, may be advanced through any suitable body lumen and body cavity, and may be used to treat tissue within any suitable body portion. For example, the apparatuses and methods described herein may be used through any natural body lumen or tract, or through incisions in any suitable tissue.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only.

We claim:

1. A method of treating tissue, the method comprising:
   delivering therapeutic energy to tissue surrounding a body lumen with a medical device;
   delivering stimulating energy to a first location proximal to, and to a second location distal to, one or more portions of tissue to which therapeutic energy was delivered, the stimulation at the first location causing a first response from tissue proximate the first location and the stimulation at the second location causing a second response from tissue proximate the second location, wherein the first location is proximal to the one or more portions of tissue relative to a longitudinal axis of the body lumen and the second location is distal to the one or more portions of tissue relative to the longitudinal axis of the body lumen; and
   applying additional therapeutic energy to the one or more portions based on a difference between the first response and the second response;
   wherein the medical device includes an expandable element and an array of contact elements, wherein the array of contact elements is configured to deliver the stimulating energy and the therapeutic energy to tissue;
   wherein the array of contact elements includes a first row of contact elements, and a second row of contact elements circumferentially spaced apart from the first row of contact elements, and delivering stimulating energy includes:
   delivering stimulating energy with only the first row of contact elements; and
   after delivering the stimulating energy with only the first row of contact elements, delivering stimulating energy with only the second row of contact elements.

2. The method of claim 1, wherein only some of the contact elements are used to deliver therapeutic energy during the step of delivering therapeutic energy.

3. The method of claim 1, wherein the medical device includes an energy delivery member having a basket, balloon, spiral, or loop shape.

4. The method of claim 1, wherein the method further includes, before the delivering therapeutic energy step:
   delivering stimulating energy from the medical device to tissue;
   detecting responses from the tissue to the stimulating energy; and
   determining one or more portions of the tissue for therapy based on the responses detected from the tissue to the stimulating energy.

5. The method of claim 4, wherein the therapeutic energy is sufficient to treat the one or more portions of tissue determined for therapy.

6. The method of claim 1, wherein the tissue is smooth muscle tissue, and the method further includes detecting electromyography (EMG) responses from the smooth muscle tissue to the stimulating energy.

7. The method of claim 1, wherein the tissue where therapeutic energy is delivered is in a first generation bronchus or a second generation bronchus.

8. The method of claim 1, wherein the stimulating energy is RF energy, and the therapeutic energy is RF energy.

9. The method of claim 1, wherein applying additional therapeutic energy to the one or more portions based on a difference between the first response and the second response includes applying additional therapeutic energy to the one or more portions when the difference between the first response and the second response is less than a threshold value.

10. A method of treating tissue, the method comprising:
delivering therapeutic energy to tissue with a medical device;
delivering stimulating energy to a first location longitudinally proximal to, and to a second location longitudinally distal to, one or more portions of tissue to which therapeutic energy was delivered, the stimulation at the first location causing a first response from tissue proximate the first location and the stimulation at the second location causing a second response from tissue proximate the second location; and
applying additional therapeutic energy to the one or more portions based on a difference between the first response and the second response;
wherein the medical device includes an expandable element and an array of contact elements, wherein the array of contact elements is configured to deliver the stimulating energy and the therapeutic energy to tissue; and wherein only some of the contact elements are used to deliver therapeutic energy during the step of delivering therapeutic energy;
wherein the array of contact elements includes a first row of contact elements, and a second row of contact elements circumferentially spaced apart from the first row of contact elements, and delivering stimulating energy includes:
delivering stimulating energy with only the first row of contact elements; and
after delivering the stimulating energy with only the first row of contact elements, delivering stimulating energy with only the second row of contact elements.

11. The method of claim 10, wherein the medical device includes an energy delivery member having a basket, balloon, spiral, or loop shape.

12. The method of claim 10, wherein the method further includes, before the delivering therapeutic energy step:
delivering stimulating energy from the medical device to tissue;
detecting responses from the tissue to the stimulating energy; and
determining one or more portions of the tissue for therapy based on the responses detected from the tissue to the stimulating energy.

13. The method of claim 10, wherein the therapeutic energy is configured to ablate the one or more portions of tissue.

14. The method of claim 10, wherein the tissue is smooth muscle tissue, and the method further includes detecting electromyography (EMG) responses from the smooth muscle tissue to the stimulating energy.

15. The method of claim 10, wherein applying additional therapeutic energy to the one or more portions based on a difference between the first response and the second response includes applying additional therapeutic energy to the one or more portions when the difference between the first response and the second response is less than a threshold value.

* * * * *